United States Patent [19]

Hancock

[11] 4,085,205

[45] Apr. 18, 1978

[54] CONTROL OF SEX RATIO IN MAMMALIAN OFFSPRING

[75] Inventor: Richard John Taylor Hancock, Bristol, England

[73] Assignee: The University Court of the University of Edinburgh, Edinburgh, Scotland

[21] Appl. No.: 761,945

[22] Filed: Jan. 24, 1977

[30] Foreign Application Priority Data

Jan. 27, 1976 United Kingdom ............... 3039/76

[51] Int. Cl.$^2$ ..................... A61K 35/52; C12K 9/00; A61K 39/00
[52] U.S. Cl. .................................... 424/105; 195/1.8; 424/85

[58] Field of Search .................. 424/105, 85

[56] References Cited

U.S. PATENT DOCUMENTS 3,687,806  8/1972   van den Bovenkamp ............ 424/85
3,692,897  9/1972   Bhattacharya ....................... 424/85

*Primary Examiner*—Sam Rosen
*Attorney, Agent, or Firm*—Howson and Howson

[57] ABSTRACT

The control of the sex ratio of mammalian offspring by the artificial insemination of a female mammal with a mixture of semen from a corresponding male mammal and serum or active serum components. The method enables the sex ratio to be controlled more economically and with less risk to the female.

5 Claims, No Drawings

CONTROL OF SEX RATIO IN MAMMALIAN OFFSPRING

The present invention seeks to provide a method of altering the relative proportions of male and female offspring conceived by mammals particularly non-human mammals.

There have been many attempts to control the sex of mammalian offspring because this would be valuable in a variety of economic conditions, for example by causing the preferential birth of female calves in dairy herds or for improving the rate of achieving superior animal strains by selective breeding. It would also be valuable medically where for example it was desired to prevent the birth of sons to mothers who are carriers of a genetic disease which affects only males.

One theoretical solution to this problem would be the addition of a specific antibody to mammalian sperm carrying, say, the male sex chromosome but one major obstacle to this is that a pure preparation of these sperm cannot as yet be separated. It has been suggested that this obstacle could be avoided when an increase in the relative proportion of female to male is desired by immunising female mammals against the sperm of birds because this sperm carries only male sex chromosomes and immunised females might therefore react preferentially against mammalian sperm carrying the male sex chromosome. Experimental work has been reported to Burkov (Vses. Konf. Fiziol. Biokhim. Osnov. Provysh. Produk. sel'skhokhoz. Zhivot., Meter 6, pages 390–391 (1968)) in which the immunising of female rabbits with cock sperm caused a decrease in the proportion of male offspring born.

However, attempts to alter the sex ratio of offspring by immunising females would be expensive and inefficient because every female would have to be immunised individually. This would be laborious and would require large amounts of antigen. Moreover the results might be rather unpredictable because the response to individual antigens varies from animal to animal and it may include undesirable effects such as anaphylactic shock.

The present invention therefore seeks to provide a more efficient and less expensive method of altering the sex ratio in mammalian offspring, by which we mean the proportions of male and female offspring born and the chance that any individual offspring will be male rather than female or vice versa.

We have now found that useful results appear to be obtained if serum is added to sperm for artificial insemination and female mammals are artificially inseminated with the resulting mixture.

According to the present invention in its broadest aspect there is provided a method of controlling the sex ratio of mammalian offspring, particularly offspring of non-human mammals, which comprises artificially inseminating female mammals with a mixture of semen from a corresponding male mammal and serum or active serum components.

As compared to the prior art proposal mentioned above the method of the present invention would be more economical in labour and in antigenic material and would involve less risk to the female.

The use of serum obtained from animals, particularly mammals, which have not been subjected to a special prior immunisation step appears to increase the proportion of males in the offspring.

Conversely, an increase in the proportion of females in the offspring can apparently be obtained if antisera against mammalian sperm bearing the male sex chromosome are added to the sperm. One means of obtaining such antisera is to employ antibodies to bird sperm because such antibodies have been found to have this effect.

According to one aspect of the invention therefore a method of increasing the proportion of females in mammalian offspring comprises artificially inseminating female mammals with a mixture of semen from a corresponding male mammal and serum or serum components containing antibodies to bird sperm.

The invention also provides a mixture of mammalian sperm and antibodies to bird sperm.

The antibodies to bird sperm may be obtained by raising them in mammals and it is expected that the mammals concerned may be those of different species from the mammals to be inseminated as well as those of the same species. The antibodies may even be raised in animals of classes other than mammals and serum containing such antibodies used in the invention. Any suitable bird species may be used as the source of the bird sperm, for example the domestic fowl. The antibodies may be obtained in the serum from the host mammals.

The use of comparative in vitro tests such as cytotoxicity tests on mammalian sperm, e.g. rabbit sperm, may be advantageous in order to select the best batches of antisera from amongst the sera. Differences have been found by in vitro cytotoxicity tests to exist between the anti-rabbit sperm activity of serum taken from a rabbit before immunisation with cock sperm and the activity of serum taken from the rabbit after immunisation with cock sperm.

For best results it is important to incubate the mixture of serum (optionally containing antibodies) and sperm for a period of time sufficient to allow the serum to interact with at least some of the sperm, and particularly to allow the antibodies to interact with at least some of the sperm bearing the male sex chromosome, prior to insemination; also to ensure that the time spent by the sperm in the female tract prior to ovulation is optimal.

Treatment of the normal serum or antiserum to separate the active components and use of these components may lead to improved results.

The following Examples illustrate the invention.

EXAMPLE 1

Rabbits were injected subcutaneously with a mixture of 25–30 × $10^8$ washed cock sperm and Freund's complete adjuvant emulsified in Tween (Registered Trade Mark) and saline according to Herbert (Handbook of Experimental Immunology, ed. DM Weir (1967)). After two injections, between 3 and 4 weeks apart, the rabbits were bled and the serum separated from the clot by centrifugation. The separated serum was heated at 56° C for 30 minutes.

The resulting antisera were added to ejaculated rabbit sperm which had been diluted in a phosphate-buffered saline solution which sometimes contained glucose, and the mixture was incubated at 37° C for about 45 minutes. The resulting product was inseminated in 1 ml portions in three separate experiments into female rabbits and ovulation was subsequently induced by intravenous injection 25 I.U. of Pregnyl (Registered Trade Mark). The concentration of sperm and dilution of antiserum in the inseminate and time interval between insemination and Pregnyl injection in the three experiments were as follows:

| Experiment No. | Concentration of sperm. | Dilution of antiserum. | Time interval |
|---|---|---|---|
| 1 | $14 \times 10^6$/ml | ½ | 90 min. |
| 2 | $28 \times 10^6$/ml | ½ | 30 min. |
| 3 | $28 \times 10^6$/ml | ½ | 1 min. |

The sex of the offspring in each case was determined by dissection.

EXAMPLE 2

Serum from unimmunised animals was mixed with ejaculated rabbit sperm and inseminated into female rabbits in the same manner as Experiment No 2 of Example 1 (concentration of sperm in inseminate $28 \times 10^6$ ml, dilution of serum ½).

The sex of the offspring in each case was determined by dissection.

The following Table gives the combined results of Experiments 1–3 of Example 1 and the results of Example 2.

|  | Number of males. | Number of females. | % of males |
|---|---|---|---|
| Example 1 | 79 | 107 | 42.5 |
| Example 2 | 50 | 28 | 64.1 |

These results therefore show a significantly reduced proportion of male offspring as a result of the use of serum from immunised animals and a significantly increased proportion of male offspring as a result of the use of serum from unimmunised animals, the expected percentage of males being 50 in each case.

What is claimed is:

1. In the artificial insemination of female mammals, a method of controlling the sex ratio of the mammalian offspring to increase the proportion of females, which comprises the steps of obtaining serum from an animal which previously has been immunized with bird sperm to cause the formation in the serum of antibodies to bird sperm, mixing semen collected from a male mammal with said antibodies to bird sperm in said serum, and artificially inseminating a corresponding female mammal with said mixture.

2. A method as claimed in claim 1, in which the mixture of semen and serum has been incubated for a period of time sufficient to allow the serum to interact with at least some of the sperm in the semen prior to insemination.

3. In the artificial insemination of female mammals, a method of controlling the sex ratio of the mammalian offspring to increase the proportion of males, which comprises the steps of obtaining serum from an animal which previously has not been immunized with sperm, mixing semen collected from a male mammal with said serum and artificially inseminating a corresponding female mammal with said mixture.

4. An inseminatory fluid comprising mammalian sperm and serum from unimmunized mammals.

5. An inseminatory fluid comprising mammalian sperm and anitbodies to bird sperm.

* * * * *